US011841356B2

(12) United States Patent
Kim (10) Patent No.: US 11,841,356 B2
(45) Date of Patent: Dec. 12, 2023

(54) LAWN MONITORING SYSTEM

(71) Applicant: Doo Soo Kim, Seoul (KR)

(72) Inventor: Doo Soo Kim, Seoul (KR)

(73) Assignee: Doo Soo Kim, Seoul (KR)

(*) Notice: Subject to any disclaimer, the term of this patent is extended or adjusted under 35 U.S.C. 154(b) by 28 days.

(21) Appl. No.: 17/608,536

(22) PCT Filed: Apr. 29, 2020

(86) PCT No.: PCT/KR2020/005646
§ 371 (c)(1),
(2) Date: Nov. 3, 2021

(87) PCT Pub. No.: WO2020/226337
PCT Pub. Date: Nov. 12, 2020

(65) Prior Publication Data
US 2022/0217930 A1    Jul. 14, 2022

(30) Foreign Application Priority Data

May 3, 2019   (KR) .................. 10-2019-0052026

(51) Int. Cl.
*G01N 33/24*   (2006.01)
*H02S 20/10*   (2014.01)
(Continued)

(52) U.S. Cl.
CPC ............. *G01N 33/24* (2013.01); *A01G 20/00* (2018.02); *A01G 25/16* (2013.01); *G01D 21/02* (2013.01);
(Continued)

(58) Field of Classification Search
CPC ...... A01G 25/167; A01G 20/00; A01G 25/16; G01D 21/02; G01N 33/24; G06Q 50/10;
(Continued)

(56) References Cited

U.S. PATENT DOCUMENTS 4,256,133 A * 3/1981 Coward ................. A01G 25/16
137/78.3
7,719,432 B1 * 5/2010 Hill ...................... G01N 33/246
73/170.16

(Continued)

FOREIGN PATENT DOCUMENTS

KR       100961837 B1 *  6/2010
KR       101184301 B1 *  9/2012
(Continued)

OTHER PUBLICATIONS

International Search Report and Written Opinion in International Appln. No. PCT/KR2020/005646, dated Sep. 4, 2020, 8 pages (with English translation).

*Primary Examiner* — Ryan D Walsh
(74) *Attorney, Agent, or Firm* — Fish & Richardson P.C.

(57) ABSTRACT

One aspect of the present invention relates to a lawn monitoring system, and more specifically, to a lawn monitoring system installed at various locations where lawn is created, such as a golf course, a soccer field, a baseball field, etc., to receive lawn status information, thereby enabling a lawn manager to manage the lawn based on the information received from the system. The lawn monitoring system according to an embodiment of the present invention has effects of accurately and efficiently transmitting the status information of the lawn in places where the lawn is created, such as a golf course, a soccer field, a baseball field, to a lawn manager.

2 Claims, 4 Drawing Sheets

(51) Int. Cl.
  *A01G 25/16* (2006.01)
  *A01G 20/00* (2018.01)
  *G01D 21/02* (2006.01)
  *H02S 10/00* (2014.01)
  *G06Q 50/10* (2012.01)

(52) U.S. Cl.
  CPC ............ *G06Q 50/10* (2013.01); *H02S 10/00* (2013.01); *H02S 20/10* (2014.12); *Y02E 10/50* (2013.01); *Y10T 137/189* (2015.04)

(58) Field of Classification Search
  CPC ......... H02S 10/00; H02S 20/10; Y02E 10/50; Y10T 137/189
  See application file for complete search history.

(56) References Cited

U.S. PATENT DOCUMENTS

| | | | | |
|---|---|---|---|---|
| 8,308,077 | B1 * | 11/2012 | Campbell | A01G 25/167 239/70 |
| 10,405,069 | B2 * | 9/2019 | Basheer | G01D 18/00 |
| 10,728,336 | B2 * | 7/2020 | Akhtar | G06Q 50/28 |
| 11,006,590 | B2 * | 5/2021 | Kumar | G01N 27/121 |
| 2004/0140902 | A1 * | 7/2004 | Staples | A01G 25/167 340/602 |
| 2005/0031416 | A1 * | 2/2005 | Bishop, Jr. | A01B 45/02 405/37 |
| 2006/0178847 | A1 * | 8/2006 | Glancy | A01G 25/167 702/62 |
| 2007/0082600 | A1 * | 4/2007 | Asvestas | A01G 9/246 454/191 |
| 2008/0129495 | A1 * | 6/2008 | Hitt | A01G 25/167 340/539.26 |
| 2011/0273196 | A1 * | 11/2011 | Hill | A01G 25/167 324/696 |

FOREIGN PATENT DOCUMENTS

| | | | |
|---|---|---|---|
| KR | 101219176 | B1 * | 1/2013 |
| KR | 20180106355 | A * | 10/2018 |
| KR | 20190006931 | A * | 1/2019 |

* cited by examiner

LAWN MONITORING SYSTEM

CROSS-REFERENCE TO RELATED APPLICATIONS

This application is a National Stage application under 35 U.S.C. § 371 of International Application No. PCT/KR2020/005646, having an International Filing Date of Apr. 29, 2020, which claims priority to Korean Application Serial No. 10-2019-0052026, filed on May 3, 2019. The disclosures of the prior applications are considered part of the disclosure of this application, and are incorporated in their entirety into this application.

TECHNICAL FIELD

The present invention relates to a lawn monitoring system, and more specifically, to a lawn monitoring system installed at various locations where lawn is created, such as a golf course, a soccer field, a baseball field, etc., to receive lawn status information, thereby enabling a lawn manager to manage the lawn based on the information received from the system.

BACKGROUND ART

The contents described in this section merely provide background information on embodiments of the present invention and it should be understood that they do not constitute the prior art.

Golf is a kind of sport in which a golf ball placed on a golf course is hit by a club, the golf ball is put into a hole cup created at a predetermined position, and the number of strokes required until that time is counted, thereby determining the ranking.

Golf is played on the golf course. The golf course is standardized using a wide area of 660,000 to 1 million square meters, such as fields, hills and forests, and there are seaside courses created on the coast and inland courses created inland.

In the golf courses, obstacles such as forests, valleys, ponds and small mountains are artificially created to control a level of difficulty. In addition, golf courses may be created using natural rivers or water bodies as they are. The golf course is generally composed of a teeing ground, the area where the golf ball is first struck, as well as fairways, roughs, bunkers, water hazards, putting greens, holes and the like.

The course and boundary of the golf course are usually marked with fences or stakes, and an outside of the boundary is referred to as an OB, and the number of holes which are holes for putting the ball therein by hitting is 18 on a regular course, which is referred to as 18 holes. In general, the first 9 holes are referred to as out courses and the latter 9 holes are referred to as in courses.

Lawn is planted and managed on the teeing ground, fairways, putting greens, and roughs of the golf course.

Lawn management is usually performed by a lawn manager belonging to the golf course.

The lawn manager of the golf course uses a lawn mower to mow the lawn created in the green area and the fairway area so as to maintain the length thereof in a set range, and sprays fertilizers or nutrients to facilitate the growth of the lawn, as well as sprays agricultural chemicals to prevent damage by blight and harmful insects.

In addition, the lawn manager uses appropriate equipment to remove damaged lawn and lay new lawn, add sand to increase the height of a layer, manage sand in bunkers designed as obstacles, manage water quality in hazard ponds, etc. Further, the lawn manager supplies water to the lawn using sprinklers, removes weeds from the lawn, and repairs equipment installed in the field.

The lawn created on the golf course varies in terms of growth states depending on conditions of the ground of the golf course, that is, temperature and humidity, salinity of the ground and the like. Therefore, maintaining the growth environment for the lawn is one of the important tasks in lawn management.

If a surface temperature of the ground of the golf course is too low or too high, lawn growth may be stopped, and in severe cases, the lawn may dry out or burn to death. If the ground of the golf course lacks nutrients, the lawn may stop growing and become vulnerable to blight and harmful insects.

The golf course has a very large area. In order to manage the lawn created in such a golf course, the lawn manager should visually confirm the large area of the golf course while directly looking around. Therefore, there are problems in that the work is overloaded, it takes a lot of time, and management costs are increased.

In addition, as described above, since the golf course is formed in various forms including the teeing ground, fairways, putting greens, and roughs, lawn management should also be accurately performed to an extent already set to suit the corresponding area. To this end, it is very difficult for the lawn manager to ascertain the state of all golf courses one by one.

SUMMARY OF INVENTION

Problems to be Solved by Invention

Accordingly, one aspect according to the present invention is proposed to solve the above-described problems, and it is an object of the present invention to provide a lawn monitoring system which accurately and efficiently transmits status information on lawn in places where the lawn is created, such as a golf course or a soccer field, to a lawn manager.

The technical problems to be solved by the present invention are not limited to the technical problems described above, other technical problems not mentioned herein will be clearly understood by those skilled in the art to which the present invention pertains.

Means for Solving Problems

To achieve the above objects, according to an aspect of the present invention, there is provided a golf course lawn monitoring system which transmit status information on lawn of a golf course to a lawn manager to efficiently manage the lawn, the system including:
  a lawn manager terminal; and
  a lawn status information transmitter,
  wherein lawn status information transmitter includes:
  a housing provided to be mounted on a ground on which the lawn is created;
  a plurality of sensors which protrude outwardly from a lower surface of the housing so as to be inserted and installed in the ground where the lawn is created, and are configured to collect temperature information, moisture information, and salinity information under the ground;
  a transmission unit which is surrounded by the housing and electrically connected to the plurality of sensors, and is configured to process the temperature information, the moisture information, and the salinity information collected by the plurality of sensors and transmit the processed information to the lawn manager terminal;

a power supply unit electrically connected to the transmission unit to supply power to the transmission unit;

a location information sending unit configured to transmit location information;

an earthquake detection unit configured to detect earthquakes;

an air quality measurement unit configured to measure fine dust and ultra-fine dust; and a protector attached and installed on an upper surface of the housing so as to be exposed on the ground on which the lawn is created in order to protect the housing and the plurality of sensors.

Herein, the power supply unit may include a solar cell module installed on an upper surface of the protector to be exposed to an outside.

In addition, the solar cell module may be installed in a stepped portion of the protector which is lowered by a predetermined depth from the upper surface of the protector to prevent damage due to a golf ball.

Further, the system may include a plurality of lawn status information transmitters, and each of the plurality of lawn status information transmitters may be installed at least one or more of green, fairway, rough, and teeing ground of each hole of the golf course.

Further, the protector may include a through hole formed therein to facilitate wireless information transmission from the transmission unit.

Advantageous Effects

As described above, the lawn monitoring system according to an embodiment of the present invention has effects of accurately and efficiently transmitting the status information of the lawn in places where the lawn is created, such as a golf course, a soccer field, or a baseball field, to a lawn manager.

In addition, the effects of the present invention have various effects such as having excellent versatility according to the embodiments, and such effects may be clearly confirmed in the description of the embodiments to be described below.

BRIEF DESCRIPTION OF DRAWINGS

The following drawings attached to the present specification illustrate an embodiment of the present invention, and serve to further understand the technical spirit of the present invention together with the detailed description of the invention, such that the present invention should not be construed as being limited only to the illustrations of the drawings.

MODE FOR CARRYING OUT INVENTION

Hereinafter, an embodiment of the present invention will be described in detail with reference to the accompanying exemplary drawings.

In denoting reference numerals to components of respective drawings, it should be noted that the same components will be denoted by the same reference numerals although they are illustrated in different drawings. In description of preferred embodiments of the present invention, the publicly known functions and configurations related to the present invention, which are judged to be able to make the purport of the present invention unnecessarily obscure will not be described in detail.

In addition, the size or shape of the components shown in the drawings may be exaggerated for the clarity and convenience of description. Further, terms specifically defined in consideration of the structure and operation of the present invention are only for describing the embodiments of the present invention, and do not limit the scope of the present invention.

Figure 1:
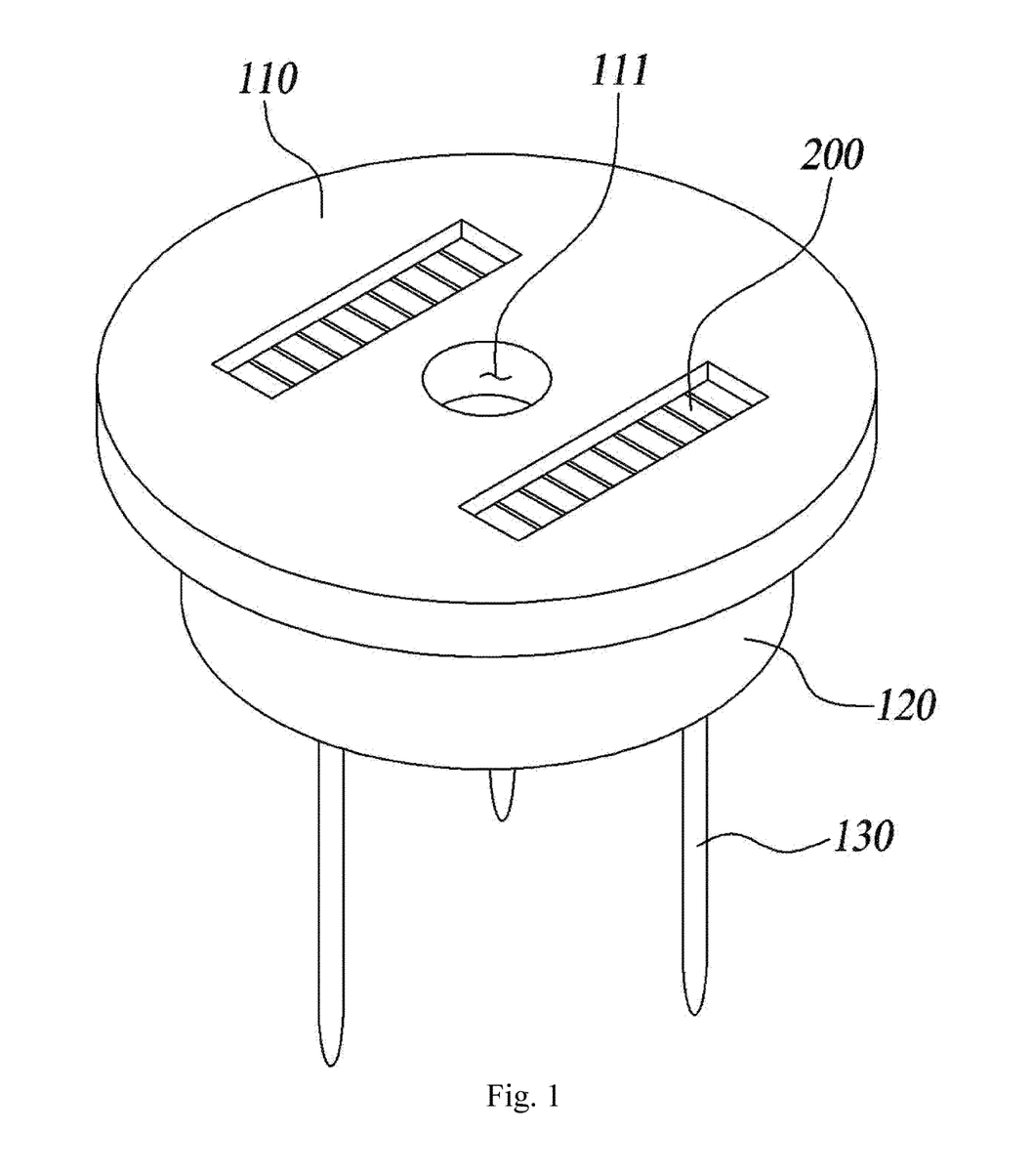
FIG. 1 is a perspective view illustrating a state of a lawn status information transmitter, which is one of components included in a lawn monitoring system according to an embodiment of the present invention.

FIG. 1 is a perspective view illustrating a state of a lawn status information transmitter, which is one of components included in a lawn monitoring system according to an embodiment of the present invention.

Figure 2:
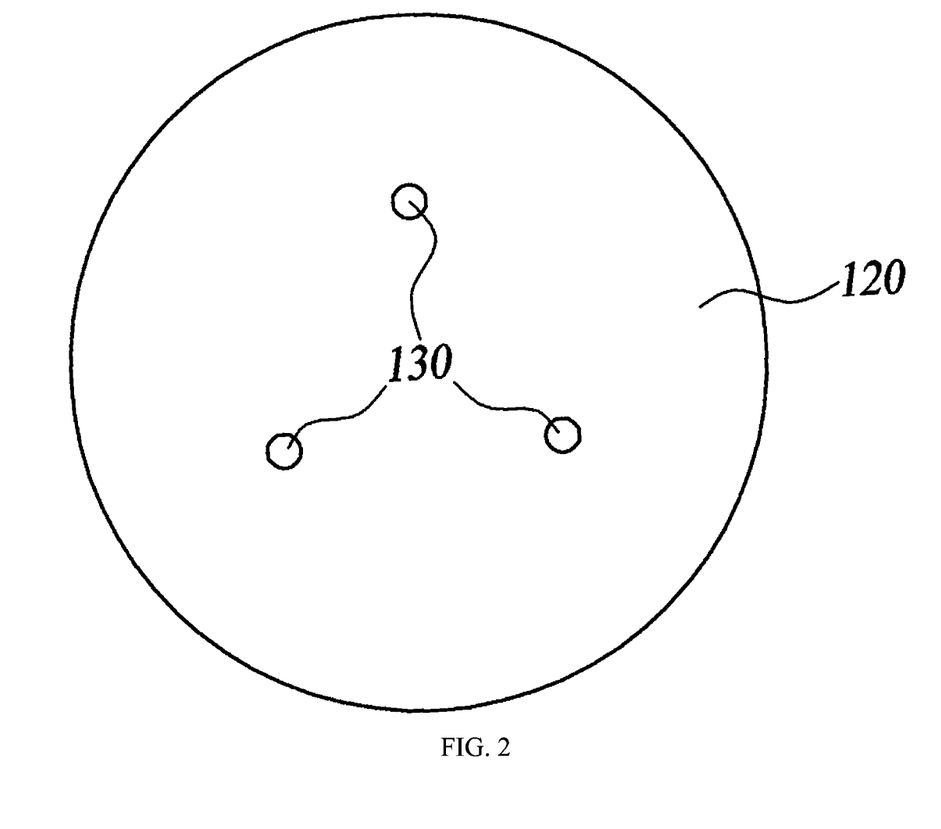
FIG. 2 is a bottom view illustrating a state in which a plurality of sensors protrude from a bottom surface of a housing of the lawn status information transmitter shown in FIG. 1.

FIG. 2 is a bottom view illustrating a state in which a plurality of sensors protrude from a bottom surface of a housing of the lawn status information transmitter shown in FIG. 1.

Figure 3:
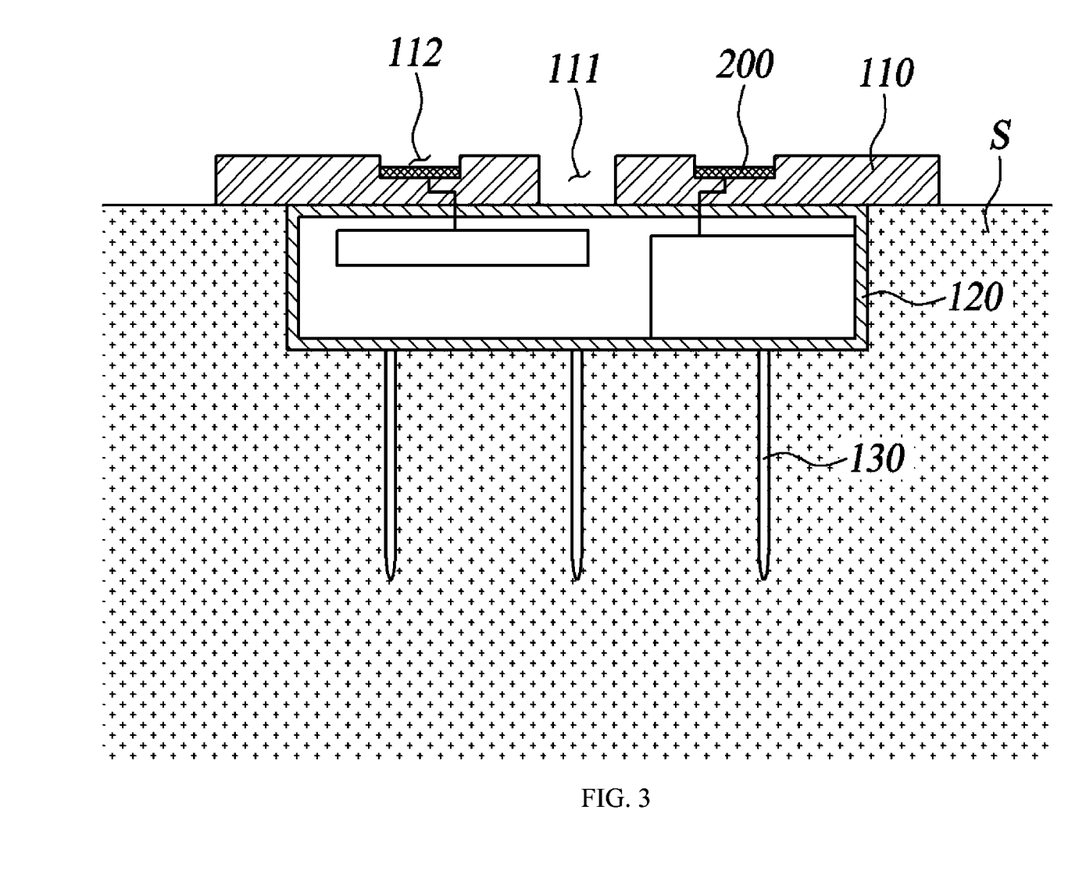
FIG. 3 is a cross-sectional view illustrating a state in which the lawn status information transmitter shown in FIG. 1 is installed on lawn.

FIG. 3 is a cross-sectional view illustrating a state in which the lawn status information transmitter shown in FIG. 1 is installed on lawn.

Figure 4:
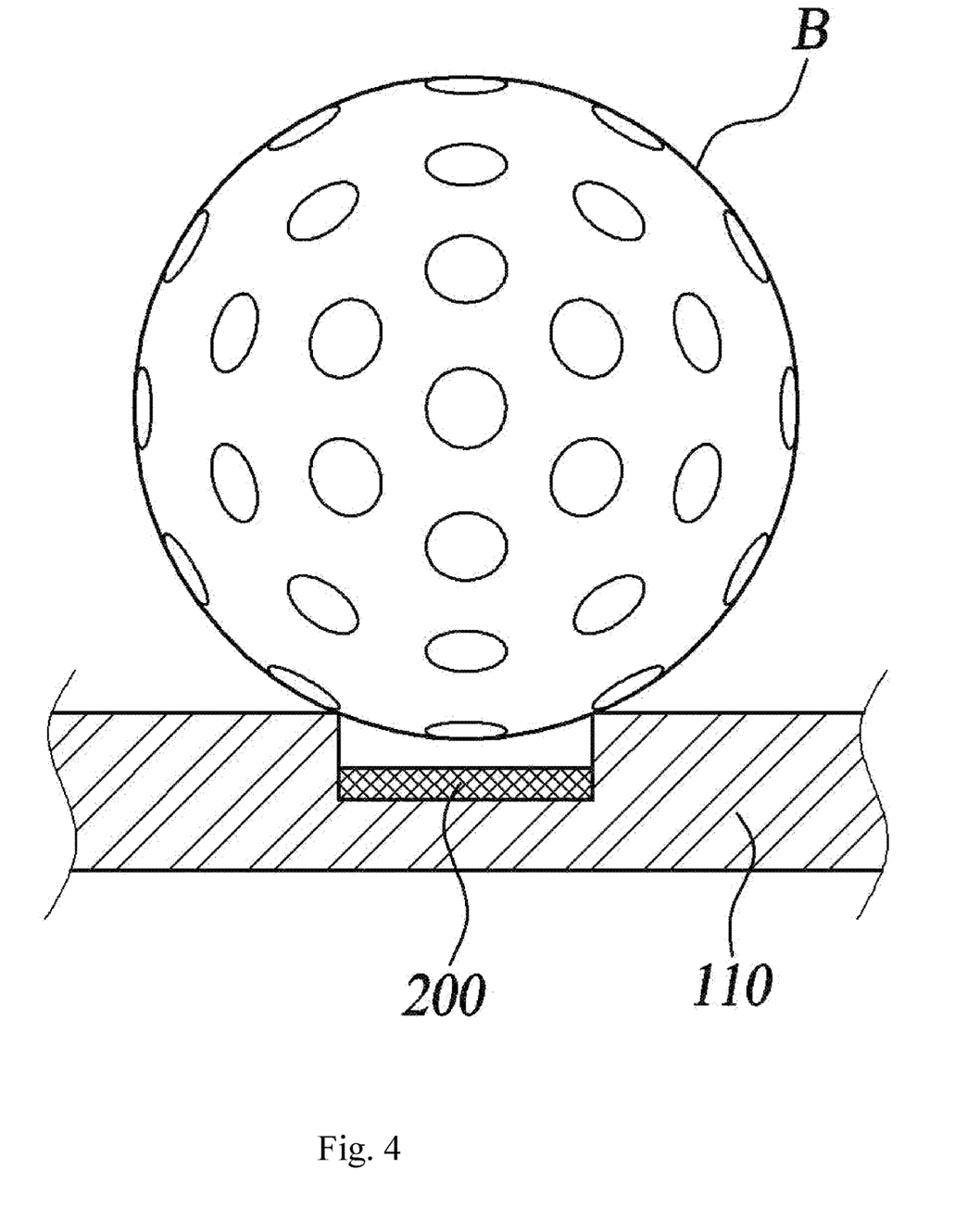
FIG. 4 is a cross-sectional view illustrating a state in which a golf ball is placed on the lawn status information transmitter then hit according to an embodiment of the present invention.

FIG. 4 is a cross-sectional view illustrating a state in which a golf ball is placed on the lawn status information transmitter then hit according to an embodiment of the present invention.

An embodiment of the present invention may provide a golf course lawn monitoring system which may transmit status information on lawn of a golf course to a lawn manager to efficiently manage the lawn.

The golf course lawn monitoring system according to the present embodiment may include a lawn manager terminal and a lawn status information transmitter 100.

The lawn manager terminal may mean a terminal which includes a memory means, and has a mobile wireless communication function and computing capability by a microprocessor equipped therewith, such as a smart phone, a tablet PC, a personal digital assistant (PDA), a web pad (Web Pad). Various applications are installed in the terminal to provide various information to the lawn manager.

In one embodiment of the present invention, the lawn manager may mean an employee who performs lawn management tasks on the golf course, but it is not limited thereto, and may mean a manager who can directly or indirectly perform the lawn management tasks on the golf course.

The lawn manager terminal and the lawn status information transmitter 100 may exchange various information and data through a wireless communication network.

The wireless communication network may include various types of data communication networks such as Metropolitan Area Network (MAN), Wide Area Network (WAN), Internet, third generation (3G) or fourth generation (4G)

mobile communication network, Wi-Fi, and Wireless Broadband Internet (WIBRO) or Long Term Evolution (LTE), and may also use any communication method known in the art.

Referring to the drawings, the lawn status information transmitter 100 of the lawn monitoring system according to an embodiment of the present invention includes: a housing 120 provided to be mounted on a ground S on which lawn is created;
- a plurality of sensors 130 which protrude outwardly from a lower surface of the housing 120 so as to be inserted and installed in the ground S where the lawn is created, and are configured to collect temperature information, moisture information, and salinity information under the ground S;
- a lawn status information transmission unit (also briefly referred to as a 'transmission unit') which is surrounded by the housing 120 and electrically connected to the plurality of sensors 130, and is configured to process the temperature information, the moisture information, and the salinity information collected by the plurality of sensors 130 and transmit the processed information to the lawn manager terminal;
- a power supply unit electrically connected to the transmission unit to supply power to the transmission unit;
- a GPS sending unit configured to transmit location information (also referred to as a 'location information sending unit') through a GPS;
- an earthquake detection unit configured to detect earthquakes;
- an air quality measurement unit configured to measure fine dust and ultra-fine dust; and
- a protector 110 attached and installed on an upper surface of the housing 120 so as to be exposed on the ground S on which the lawn is created in order to protect the housing 120 and the plurality of sensors 130.

The housing 120 is formed to surround a printed circuit board (PCB) on which the transmission unit, a part of the power supply unit, the GPS sending unit, the earthquake detection unit, and the air quality measurement unit are integrally mounted. The housing 120 may be made of a plastic material, but the material thereof is not limited thereto.

The housing 120 is molded to be closed with an outside as a whole. According to an embodiment, the housing may be formed in a form of assembling one case with the other case.

The plurality of sensors 130 are assembled to protrude from a bottom surface of the housing 120. The plurality of sensors 130 may include a temperature sensor for collecting temperature information, a humidity sensor for collecting humidity information, and a salinity sensor for collecting salinity information. The temperature information, humidity information, and salinity information are basic lawn status information indicating lawn conditions, and the plurality of sensors 130 collects these information.

The protector 110 may be attached and installed on the upper surface of the housing 120. When the lawn status information transmitter 100 is installed on the lawn of a golf course, the protector 110 functions to prevent the housing 120 from being damaged due to an impact of a golfer or a golf ball. The protector 110 may be made of impact-resistant reinforced plastic or metal.

Meanwhile, a golf course lawn management application for providing information on the lawn condition of the golf course according to the present invention may be installed in the lawn manager terminal according to the present embodiment. In addition, the lawn manager terminal may receive and display information related to the lawn condition of the golf course and location information of a point corresponding to the lawn status information from the lawn status information transmitter 100.

The golf course lawn management application may be set to perform a warning function to the lawn manager. The warning may be issued when the temperature information, moisture information, and salinity information are out of a set temperature range, moisture range, and salinity range, respectively.

For example, when the temperature of the soil, in which the lawn is created, is maintained at a temperature between a set first temperature and a second temperature higher than the first temperature, only temperature information is displayed on the lawn manager terminal or the lawn management server at a constant time interval. However, when the soil temperature is lower than the first temperature or higher than the second temperature, a warning may be issued to the lawn manager through the lawn manager terminal. A manner of issuing the warning may be carried out in a visual, audible or tactile manner. For example, the visual method may display a visual warning on the lawn manager terminal in a push notification method.

Herein, the first temperature and the second temperature are values set in advance, and may mean 10 degrees Celsius and 18 degrees Celsius, respectively, according to an embodiment, and a warning may be issued when the temperature of the soil is less than 10 degrees Celsius or exceeds 18 degrees Celsius.

In addition, a warning may also be issued when the moisture information falls below a set moisture content, and a warning may also be issued when the salinity information is out of a set salinity range. The lawn manager may confirm the above information through the lawn manager terminal, and may irrigate the lawn or supply appropriate nutrients at the right time and in the correct area.

The uploaded lawn status information may be accumulated in the lawn manager terminal. That is, when an information value, which is accumulated and stored like a graph or an Excel table and is out of a set range, is uploaded, a display color may be set to change with respect to the information value.

For example, when the temperature is 15 degrees Celsius, the display color is displayed as a basic color, but when the temperature is out of the set temperature range, the display color may be changed, for example, to be displayed in red. For example, if the temperature information is 19 degrees Celsius, the display color may be displayed in red. In this case, at the same time, a push alarm is operated in the form of a pop-up window on the lawn manager terminal, and the situation is automatically communicated to the lawn manager, such that the lawn manager may immediately start the lawn management task.

In addition, when the soil temperature is maintained at a temperature between the first temperature and the second temperature higher than the first temperature, only temperature information may be displayed on the lawn manager terminal in a chart format such as a graph or Excel table. However, when the soil temperature is lower than the first temperature or higher than the second temperature, a visual warning may be issued by changing the display color using a highlight method or the like with respect to the abnormal temperature.

In this case, a plurality of lawn status information transmitters 100 may be provided in the system, and the plurality of lawn status information transmitters 100 are disposed for each hole of the golf course. That is, the lawn status information transmitters 100 are installed and disposed in a teeing ground area, a fairway area, a rough area, and a putting green area of each hole.

According to an embodiment, the lawn status information transmitter 100 may be installed in a manner that the protector 110 portion is exposed on the ground S, and the plurality of sensors 130 and the housing 120 are installed under the ground S. The protector 110 made of a rigid material may be mounted like a manhole cover on the ground S on which the lawn is created, and the plurality of sensors 130 are installed so that ends thereof are positioned at a predetermined depth in the ground S. That is, the end of the sensor may be designed to be positioned between 10 cm to 20 cm from the ground S.

If the end of the sensor is located at a depth of less than 10 cm from the ground S, it may be lost due to an impact during hitting a golf ball B by a golfer, and if it is located at a depth of 20 cm or more, it may be difficult to send the status information up to the ground.

The plurality of lawn status information transmitters 100 may be disposed in consideration of the growth conditions of the lawn. One of the growing conditions is an amount of sunlight.

A location where the plurality of lawn status information transmitters 100 are disposed in one hole may be determined according to the amount of sunlight. For example, when an inclined surface is formed by undulation of a fairway, the amount of sunlight varies depending on the direction, inclination, etc. of the inclined surface, and a difference in the amount of sunlight directly affects the growth of lawn. Therefore, the installation position and disposition structure of the lawn status information transmitter 100 may be determined in consideration of the direction and the inclination of the inclined surface.

Further, for example, when the ground is shaded by a forest, grasses, trees, etc. in the fairway, the shaded point has a difference in the amount of sunlight compared to other points, such that the growth conditions of the lawn created at the corresponding point are different. Accordingly, the installation location of the lawn status information transmitter 100 may be determined in consideration of the location of the forest, grasses, trees and the like.

According to an embodiment of the method of arranging the lawn status information transmitters 100 in consideration of the amount of sunlight, they may be installed respectively at a point where a difference in the amount of sunlight greater than or equal to a set value occurs. For example, when the inclined surface is formed by undulation of the fairway, a difference in the amount of sunlight occurs between the inclined surface and a flat land. If the difference is greater than the set value, one lawn status information transmitter 100 may be disposed on each of the inclined surface and the flat land. In this case, the number of installed lawn status information transmitters 100 may be determined at the fairway point in consideration of the amount of sunlight.

The transmission unit according to the present invention requires power in order to transmit the lawn status information collected by the plurality of sensors 130 to the outside. In order to receive this power, the power supply unit may be installed inside the housing 120 according to the embodiments. The power supply unit may be a battery or may include a solar cell module 200 according to the embodiments.

The power supply unit according to an embodiment of the present invention is installed on the upper surface of the protector 110, and may include the solar cell module 200 installed to be exposed to the outside. Therefore, the solar cell module 200 absorbs solar energy and converts it into electric power, then may supply the power to the PCB including the transmission unit, etc. mounted thereon. Since the transmission unit consumes a very small amount of power, the solar cell module 200 does not need to be large.

According to an embodiment, the solar cell module 200 may be installed in a stepped portion 112 of the protector 110 which is lowered by a predetermined depth from the upper surface of the protector 110 to prevent damage due to a golf ball. An interval between one side and the other side of the stepped portion 112 is not limited, and it is sufficient so long as it does not touch the solar cell module 200 even if it is hit by the golf ball B.

A through hole 111 may be formed in the protector 110 of the present invention to facilitate transmission of wireless information from the transmission unit. In terms of a depth, it is sufficient that the through hole 111 is formed in such a way that the upper surface and the bottom surface of the protector 110 communicate with each other so that a portion of the upper surface of the housing 120 disposed on the bottom surface of the protector 110 can be exposed to the outside. The through hole 111 may be formed at any position in the protector 110. However, it is more preferable to be positioned close to a portion where the signal is transmitted.

According to an embodiment of the present invention, the lawn status information transmission unit may further include a location information sending unit configured to transmit location information, an earthquake detection unit configured to detect earthquakes, or an air quality measurement unit configured to measure fine dust and ultrafine dust.

The location information sending unit may transmit location information of the lawn status information transmitter 100 in a GPS method according to the embodiments. However, the location information transmission method is not limited to the GPS method.

The lawn status information transmitter 100 transmits its own location information, and thereby it may notify that the transmitted lawn status information is information on the lawn created at any position of the golf course.

In addition, the lawn status information transmission unit according to an embodiment of the present invention includes the earthquake detection unit for detecting earthquakes so that natural disasters can be confirmed in advance, and the air quality measurement unit for measuring the fine dust and ultrafine dust. Therefore, in the case of dusty or poor air quality, the golf course or golfer may take appropriate action before the round based on the measured air quality.

The earthquake detection unit and the air quality measurement unit may also transmit earthquake information and pollution information such as fine dust to a national safety net server.

Meanwhile, the lawn status information transmitter 100 according to the present invention may transmit information on the amount of sunlight to the lawn manager terminal. Since the amount of sunlight affects the growth of lawn, it is possible to confirm the condition of the lawn by analyzing the information on the amount of sunlight.

The information on the amount of sunlight may be collected through the solar cell module 200 in the present embodiment, according to the embodiments. The lawn status information transmitter 100 according to the present invention may transmit solar energy information absorbed by the solar cell module 200 and power consumption information consumed by the PCB including the transmission unit, etc. mounted thereon.

A program installed in the lawn manager terminal may analyze a difference value between the amount of solar energy per unit time, which is information received by the solar cell module 200 from the lawn status information transmitter 100, and the power consumption of the PCB including the transmission unit, etc., to generate the information on the amount of sunlight. Thus, it is possible to confirm the conditions of the lawn through the generated information on the amount of sunlight.

The above description is merely illustrative of the technical idea of the present invention, and those skilled art to which the present invention pertains will appreciate that various modifications and variations are possible without departing from the essential characteristics of the present invention.

Therefore, the embodiments disclosed in the present invention are intended to describe the technical idea of the present invention, and are not intended to limit the same, as well as the scope of the technical idea of the present invention is not limited to these embodiments.

It should be understood that the protective scope of the present invention is interpreted by the claims below, and all technical ideas within the equivalent range are included in the scope of the present invention.

The invention claimed is:

1. A golf course lawn monitoring system which transmit status information on lawn of a golf course to a lawn manager to efficiently manage the lawn, the system comprising:
   a lawn manager terminal; and
   a lawn status information transmitter,
   wherein the lawn status information transmitter comprises:
   a housing provided to be mounted on a ground on which the lawn is created;
   a plurality of sensors which protrude outwardly from a lower surface of the housing so as to be inserted and installed in the ground where the lawn is created, and are configured to collect temperature information, moisture information, and salinity information under the ground;
   a transmission unit which is surrounded by the housing and electrically connected to the plurality of sensors, and is configured to process the temperature information, the moisture information, and the salinity information collected by the plurality of sensors and transmit the processed information to the lawn manager terminal;
   a power supply unit electrically connected to the transmission unit to supply power to the transmission unit;
   a location information sending unit configured to transmit location information;
   an earthquake detection unit configured to detect earthquakes;
   an air quality measurement unit configured to measure fine dust and ultra-fine dust; and
   a protector attached and installed on an upper surface of the housing so as to be exposed on the ground on which the lawn is created in order to protect the housing and the plurality of sensors,
   wherein the power supply unit includes a solar cell module installed on an upper surface of the protector to be exposed to an outside,
   wherein the solar cell module is installed in a stepped portion of the protector which is lowered by a predetermined depth from the upper surface of the protector to restrict damage due to a golf ball,
   wherein the system further comprises a plurality of lawn status information transmitters, and each of the plurality of lawn status information transmitters is installed at least one of green, fairway, rough, or teeing ground of each hole of the golf course,
   wherein the lawn manager terminal is configured to execute a golf course lawn management application for providing information on a lawn condition of the golf course, the lawn manager terminal being configured to receive and display information related to the lawn condition of the golf course and location information of a point corresponding to lawn status information from the lawn status information transmitter,
   wherein the golf course lawn management application is configured to perform a warning function to the lawn manager, the warning function including issuing a warning based on at least one of the temperature information being out of a set temperature range, the moisture information being out of a set moisture range, or the salinity information being out of a set salinity range,
   wherein, based on temperature of a soil having the lawn being maintained at a temperature between a first temperature and a second temperature higher than the first temperature, at least one of the lawn manager terminal or a lawn management server is configured to display only temperature information at time intervals,
   wherein, based on the temperature of the soil having the lawn being lower than the first temperature or higher than the second temperature, the lawn manager terminal is configured to issue a warning to the lawn manager in a visual, audible or tactile manner,
   wherein, based on the moisture information falling below a set moisture content, the lawn manager terminal is configured to issue a warning,
   wherein, based on the salinity information being out of a set salinity range, the lawn manager terminal is configured to issue a warning,
   wherein an installation position of each of the plurality of lawn status information transmitters is determined based on an amount of sunlight that varies according to a direction and an inclination of a surface having the lawn, and each of the plurality of lawn status information transmitters is installed respectively at a point where a difference in the amount of sunlight is greater than or equal to a set value,
   wherein each of the plurality of lawn status information transmitters is configured to transmit information on the amount of sunlight to the lawn manager terminal, each of the plurality of lawn status information transmitters being configured to transmit (i) information of solar energy absorbed by the solar cell module and (ii) information of power consumption consumed by the transmission unit, and
   wherein a program installed in the lawn manager terminal is configured to analyze a difference value between (i) an amount of the solar energy received by the solar cell module from the lawn status information transmitter and (ii) the power consumption of the transmission unit.

2. The system according to claim 1, wherein the protector includes a through hole formed therein to facilitate wireless information transmission from the transmission unit.

* * * * *